United States Patent [19]

Dowling et al.

[11] 4,059,987
[45] Nov. 29, 1977

[54] APPARATUS AND METHOD FOR MEASURING THE WATER CONTENT OF OIL FLOWING IN A PIPE

[75] Inventors: Donald J. Dowling, Houston; William Schoen, Missouri City, both of Tex.

[73] Assignee: Texaco Inc., New York, N.Y.

[21] Appl. No.: 734,060

[22] Filed: Oct. 20, 1976

[51] Int. Cl.² .......................................... G01N 25/58
[52] U.S. Cl. .............................................. 73/61.1 R
[58] Field of Search ........................ 73/73, 61.1 R

[56] References Cited

U.S. PATENT DOCUMENTS

| | | | |
|---|---|---|---|
| 3,359,787 | 12/1967 | Zemawek | 73/61.1 R |
| 3,498,112 | 3/1970 | Howard | 73/61.1 R |
| 3,859,846 | 1/1975 | Asada et al. | 73/61.1 R |
| 3,892,127 | 7/1975 | Cirulis et al. | 73/61.1 R |

*Primary Examiner*—James J. Gill
*Assistant Examiner*—Anthony V. Ciarlante
*Attorney, Agent, or Firm*—Thomas H. Whaley; Carl G. Ries; Ronald G. Gillespie

[57] ABSTRACT

Apparatus and method for measuring oil flowing in a pipe include continuously sampling the oil to provide a stream of sample oil. The temperature of the sample oil is changed by a predetermined amount. The acoustical velocity of the sample oil is determined prior to the temperature change and after the temperature change by sensors providing corresponding signals. A circuit provides a signal corresponding to the water content of the oil in accordance with the acoustical velocity and the known temperature change.

8 Claims, 2 Drawing Figures

APPARATUS AND METHOD FOR MEASURING THE WATER CONTENT OF OIL FLOWING IN A PIPE

BACKGROUND OF THE INVENTION

Field of the Invention

The present invention relates to measuring apparatus and methods in general and, more particularly, to apparatus and method for measuring the water content of oil.

SUMMARY OF THE INVENTION

Apparatus which measures the water content of oil flowing in a pipe includes continuously sampling the oil to provide a stream of sample oil, equipment having a stream of sample oil passing through it changes the temperature of the sample oil by a predetermined amount. Transducers on either side of the equipment determines the acoustical velocity of the stream sample oil prior to the temperature change and after the temperature change and provide corresponding signals. A network connected to the sensors provides a signal corresponding to the water content of the oil in accordance with the signals from the sensors and the predetermined temperature change.

The objects and advantages of the invention will appear more fully hereinafter from a consideration of the detailed description which follows, taken together with the accompanying drawings wherein one embodiment of the invention is offered by way of example. It is to be expressly understood, however, that the drawings are for illustration purposes only and are not to be construed as defining the limits of the invention.

DESCRIPTION OF THE INVENTION

Figure 1:
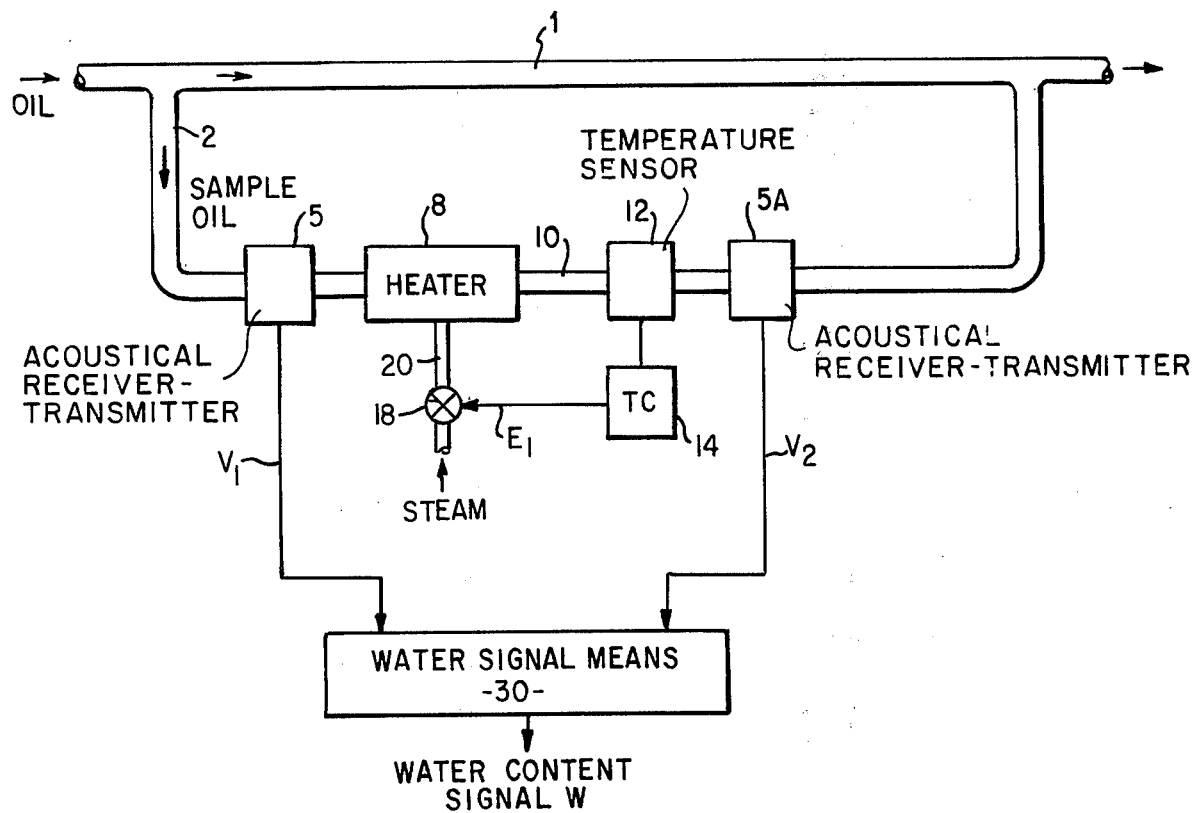
FIG. 1 is a partial simplified block diagram and a partial schematic diagram of apparatus constructed in accordance with the present invention for measuring the water content of oil flowing in a pipe.

Referring now to FIG. 1, oil in a pipeline is continuously sampled by way of another line 2 wherein an acoustical receiver-transmitter 5, which may be of a conventional type, provides a signal V1 corresponding to the acoustical velocity of the sample oil in line 2. The sample oil is provided to a heater 8 wherein the sample oil is heated by a predetermined amount and provided to another line 10. Situated in line 10 is a conventional temperature sensor 12 and a temperature controller 14 which in turn provides a control signal E1 to a valve 18 in a steam line 20 so as to control the heating of the sample oil to increase the sample oil temperature by a predetermined amount. It should be noted that although the present embodiment is shown heating the oil by a predetermined amount, it could just as well be shown as decreasing the temperature of the sample oil by a predetermined amount. The heated sample oil in line 10 has its acoustical velocity sensed by another receiver transmitter 5A which provides a signal V2 corresponding to the acoustical velocity of the heated sample oil in line 10. An element identified with number and a suffix is identical to an element having the same number but no suffix.

Receiver-transmitters 5, 5A provide signals V1 and V2, respectively, to water signal means 30 which provides signal W, corresponding to the water content in accordance with signals V1, V2 and the known predetermined temperature change.

Figure 2:
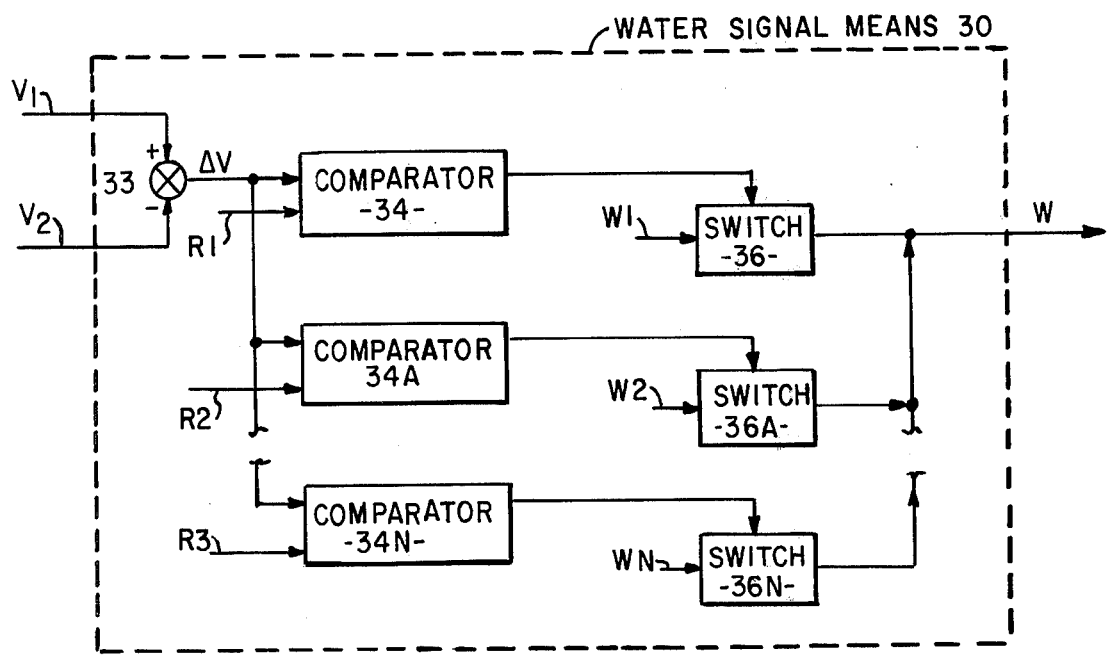
FIG. 2 is a detailed block diagram of the water signal means shown in FIG. 1.

Referring to FIG. 2, subtracting means 33 in water signal means 30 subtracts signal V2 from signal V1 to provide a signal $\Delta V$ corresponding to the change in acoustical velocity of the sample oil due to the temperature change. Signal $\Delta V$ is applied to comparators 34, 34A and 34N. The break in the $\Delta V$ signal line between comparator 34A and comparator 34N indicates any number of comparators may be utilized but only three are shown for convenience. Comparators 34, 34A and 34N receive reference signals R1, R2 and RN, respectively, corresponding to different values for signal $\Delta V$. In effect, comparators 34, 34A and 34N determine the amplitude level of signal $\Delta V$. Comparators 34, 34A and 34N provide control signals to switches 36, 36A and 36N, respectively, receiving direct current voltages W1, W2 and WN, respectively. Voltages W1, W2 and WN correspond to predetermined values of water content in oil for various changes $\Delta V$ in the acoustical velocity of the oil due to the known temperature change. It is obvious that there can be numerous combinations of values since the value of the temperature change may be different. However, it is only necessary to set up one set of values for a particular oil type and a particular temperature change. The outputs of switches 36, 36A and 36N are tied to a common point so that the control signals from comparators 34, 34A, 34N will render one of the switches conductive to pass that particular voltage applied to it as signal W.

Signal W may be recorded. It may also be used as a control signal whereby when signal W reaches a certain value it will in turn stop the oil flowing in line 1 since it contains too much water all of which is not shown but would be obvious to one skilled in the art.

The present invention as hereinbefore described is apparatus and method of measuring the water content of oil flowing in a line. The oil is continuously sampled to provide sample oil which has its temperature changed by a predetermined amount. The acoustical velocity of the sample oil is sensed prior to and after the temperature change and the water content is determined in accordance with the sensed acoustical velocities and the known temperature change.

What is claimed is:

1. Apparatus for providing an output corresponding to the water content of oil flowing in a pipe comprising means for continuously sampling the oil to provide a stream of sample oil, means for changing the temperature of the sample oil by a predetermined amount, means for measuring the acoustical velocity of the sample oil prior to the temperature change and after the temperature change and providing corresponding signals, and output means connected to acoustical velocity sensing means for providing the output corresponding to the water content of the oil in accordance with the signals from the acoustical velocity sensing means and the known predetermined temperature change.

2. Apparatus as described in claim 1 further comprising means for returning the sample oil to the pipe.

3. Apparatus as described in claim 2 in which the output means includes means for providing a signal corresponding to the difference between the sensed acoustical velocities, means for providing a plurality of water content signals, each water content signal corresponds to a different water content of oil associated with a corresponding acoustical velocity change for the predetermined temperature change, and means connected to the difference signal means and to the water content signal means for selecting one of the water content signals in accordance with the difference signal and providing the selected signal as the output.

4. Apparatus as described in claim 3 in the selecting means includes reference signal means for providing a plurality of reference signals, each reference signal corresponding to a different value for the difference signal, comparator means, each comparator means receiving a different reference signal from the reference signal means and connected to the difference signal means for providing a comparison signal in accordance with the comparison of the difference signal with the reference signal, and plurality of switches having a common output connection, each switch being connected to a corresponding comparator and receiving a water content signal, associated with the reference signal provided to the comparator, from the water signal means and controlled by the comparison signal to pass the water content signal to the common output or to block the water content signal.

5. A method for providing an output corresponding to the water content of oil flowing in a pipe which comprises continuously sampling the oil to provide a stream of sample oil, changing the temperature of the sample oil by a predetermined amount, measuring the acoustical velocity of the sample oil prior to the temperature change and after the temperature change, providing signals corresponding to the measured velocities, and providing the output corresponding to the water content of the oil in accordance with the velocity signals and the known predetermined temperature change.

6. A method as described in claim 5 which further comprises returning the sample oil to the pipe.

7. A method as described in claim 6 in which the output step includes providing a signal corresponding to the difference between the sensed acoustical velocities in accordance with the velocity signals, providing a plurality of water content signals, each water content signal corresponds to a different water content of oil associated with a corresponding acoustical velocity change for the predetermined temperature change, and selecting one of the water content signals in accordance with the difference signal and providing the selected signal as the output.

8. A method as described in claim 7 in the selecting step includes providing a plurality of reference signals, each reference signal corresponding to a different value for the difference signal, comparing each reference signal with the difference signal to provide corresponding comparison signals, and providing one of the water content signals as the output in accordance with the comparison signals.

* * * * *